United States Patent [19]

Lachhein et al.

[11] Patent Number: 4,792,610

[45] Date of Patent: Dec. 20, 1988

[54] PROCESS FOR THE PREPARATION OF 5-PHENYLSULFINYL-1H-2-(METHOXYCARBONYLAMINO)-BENZIMIDAZOLE

[75] Inventors: Stephen Lachhein, Hofheim am Taunus; Hilmar Mildenberger, Kelkheim (Taunus); Hans-Joachim Ressel, Hattersheim am Main, all of Fed. Rep. of Germany

[73] Assignee: Hoechst Aktiengesellschaft, Fed. Rep. of Germany

[21] Appl. No.: 80,087

[22] Filed: Jul. 31, 1987

[30] Foreign Application Priority Data

Jun. 13, 1987 [DE] Fed. Rep. of Germany ....... 3719783

[51] Int. Cl.$^4$ .................. C07D 235/30; C07D 235/32
[52] U.S. Cl. ..................................................... 548/329
[58] Field of Search ......................................... 548/329

[56] References Cited

U.S. PATENT DOCUMENTS

| | | | |
|---|---|---|---|
| 3,480,643 | 11/1969 | Lutz et al. | 548/329 |
| 3,929,821 | 12/1975 | Beard et al. | 260/309.2 |
| 3,929,822 | 12/1975 | Beard et al. | 260/309.2 |
| 3,929,824 | 12/1975 | Beard et al. | 260/309.2 |
| 4,197,307 | 4/1980 | Gallay et al. | 548/329 |
| 4,255,431 | 3/1981 | Junggren et al. | 548/329 |

FOREIGN PATENT DOCUMENTS

| | | | |
|---|---|---|---|
| 1210015 | 7/1986 | Canada | 548/329 |
| 0091052 | 3/1983 | European Pat. Off. | 548/329 |
| 2363351 | 7/1974 | Fed. Rep. of Germany | 548/329 |
| 2334631 | 8/1975 | Fed. Rep. of Germany | 548/329 |
| 2432631 | 1/1976 | Fed. Rep. of Germany | 548/329 |
| 1428933 | 3/1976 | United Kingdom | 548/329 |
| 1434830 | 5/1976 | United Kingdom | 548/329 |

OTHER PUBLICATIONS

AA:Undheim et al., Acta Chem. Scand., 24, No. 9 (1970), 3429–3430.

Hoggarth, The Preparation and Reactivity, etc., J. Chem. Soc. 1949, pp. 3311–3315.

Primary Examiner—Alan L. Rotman
Assistant Examiner—J. Richter
Attorney, Agent, or Firm—Finnegan, Henderson, Farabow, Garrett, & Dunner

[57] ABSTRACT

A highly selective, inexpensive and quantitative process is described for the preparation of 5-phenylsulfinyl-1H-2-(methoxycarbonylamino)-benzimidazole (oxfendazole) through reaction of 5-phenylmercapto-1H-2-(methoxycarbonylamino)-benzimidazole with hydrogen peroxide in the presence of one or more aliphatic $C_1$-$C_6$-alcohols with addition of a strong, nonoxidizing mineral acid.

7 Claims, No Drawings

PROCESS FOR THE PREPARATION OF 5-PHENYLSULFINYL-1H-2-(METHOXYCARBONYLAMINO)-BENZIMIDAZOLE

5-Phenylsulfinyl-1H-2-(methoxycarbonylamino)-benzimidazole (abbreviation: oxfendazole) of the formula I is a valuable anthelmintic with a broad spectrum of action which is highly suitable for combating parasitic disorders in humans and animals (German Patent No. 2,363,351).

For the preparation of, for example, 5-phenylsulfinyl-1H-2-(methoxycarbonylamino)-benzimidazole I

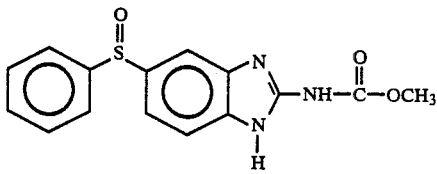

5-phenylmercapto-1H-2-(methoxycarbonylamino)-benzimidazole (abbreviation: fenbendazole) II

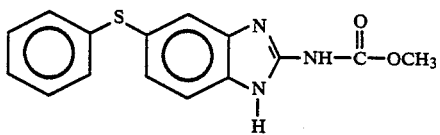

is reacted with hydrogen peroxide in acetic acid (German Offenlegungschrift No. 2,334,631 and German Offenlegungssschrift No. 2,432,631). The disadvantage of this procedure is the 5-phenylsulfonyl-1H-2-(methoxycarbonylamino)benzimidazole formed as a byproduct by overoxidation.

It is known that thioethers in general can be oxidized using hydrogen peroxide in organic acids, such as, for example, formic acid, to form the sulfoxide (K. Undheim, Act. Chem. Scand., 24, (1970), 3429).

Furthermore, the oxidation of thioethers using hydrogen peroxide in methanol is described (J. Drabowicz et al., Synth. Commun. 11(12), (1981), pp. 1025 ff). However, selective oxidations (no sulfone formation) and high yields are obtained only in the synthesis of dialkyl and arylalkyl sulfoxides. This process is not suitable for the oxidation of diaryl thioethers.

In addition, oxidation succeeds using oxidizing acids, such as nitric acid (Houben-Weyl, Vol. 4/1a (1981), pp. 736 ff) and $H_2O_2$/sulfuric acid (EP-A No. 91,052). The disadvantages of these oxidation processes are the formation of the sulfone (overoxidation →low selectivity as an undesired byproduct and the frequently very poor yields (G. Barbieri et al., J. Chem. Soc.[C], (1968), p. 659).

Selective oxidations only succeed in high yields using expensive reagents, such as, for example, titanium trichloride (Y. Watanabe et al., Synthesis, (1981), p. 204) and bromine in a two-phase system with chlorinated hydrocarbons (J. Drabowicz et al., Synthesis, (1979), p. 39).

The present invention relates to a highly selective, inexpensive and simple process for the preparation of 5-phenylsulfinyl-1H-2-(methoxycarbonylamino)-benzimidazole (I).

It has surprisingly now been found that, for heterocyclic thioethers, a highly selective reaction course is obtained in a quantitative yield when the oxidation reaction is carried out using hydrogen peroxide in the presence of aliphatic alcohols using a nonoxidizing mineral acid.

The invention therefore relates to a process for the preparation of oxfendazole through reaction of 5-phenylmercapto-1H-2-(methoxycarbonylamino)-benzimidazole with hydrogen peroxide, wherein the reaction is carried out in mineral acid in the presence of one or more aliphatic $C_1$-$C_6$-alcohols.

The process according to the invention is particularly distinguished by the fact that the total amount of hydrogen peroxide at the start of the reaction can be added in one portion to the reaction mixture. In spite of this large excess of hydrogen peroxide, no 5-phenylsulfonyl-1H-2-(methoxycarbonylamino)-benzimidazole is formed under these conditions from the resultant sulfoxide (oxfendazole).

The particular advantage of this process is thus that there is a completely free choice of the mode of addition of the oxidant, which is of decisive importance with respect to an industrial procedure.

Important aliphatic alcohols are, for example, $C_1$-$C_6$-alkanols, particularly methanol.

Suitable mineral acids are nonoxidizing acids, such as, for example, hydrochloric acid, hydrobromic acid and phosphoric acid.

The oxidant used is hydrogen peroxide, which can be employed in an equimolar amount and in an excess of up to twice the equimolar amount. The pH range and the temperature range can vary within broad limits. However, the process is preferably carried out at a pH between $-1.0$ and 2.0 and a reaction temperature of 0° to 80° C.

To carry out the reaction, 5-phenylmercapto-1H-2-(methoxycarbonylamino)-benzimidazole is expediently dissolved or slurried in the alcohol, and the nonoxidizing mineral acid is added at 0° C. to 80° C., preferably at 20° C. to 60° C., a pH of $-1.0$ to 2.0, preferably 0 to 1.5, being produced. The addition can also be carried out in the reverse sequence. The equimolar to twice the equimolar amount of hydrogen peroxide is then added. The hydrogen peroxide is employed as a 5 to 50% strength aqueous solution and can be added in the entire amount at the beginning of the reaction or in any number of portions over the entire course of the experiment.

It is furthermore expedient to carry out the process under an inert gas atmosphere, for example under nitrogen, in order to avoid the interfering effects of oxygen on the reaction.

The process according to the invention is distinguished by the fact that the oxidation of thioethers to the sulfoxide proceeds completely selectively (without sulfone formation) and quantitatively, and the formation of the sulfoxide is not dependent on the mode of addition of the oxidant. No organic acids are used. The waste water is not toxic to fish and can easily be catabolized. The oxfendazole obtained meets the specification.

The process according to the invention is described below with reference to several examples.

EXAMPLE 1

61.7 g of a 35% strength hydrogen peroxide solution, diluted in 62 g of water, are added dropwise within 2 hours under a nitrogen atmosphere to a solution of 186.4 g of fenbendazole in 750 ml of methanol, 250 g of concentrated hydrochloric acid and 630 ml of water at 50° C. and a pH of 0.3–0.4.

The reaction mixture is stirred for a further 6 hours at 50° C., and 3.0 g of sodium sulfite are added. After cooling to room temperature, the reaction mixture is diluted with 600 g of water, and the pH is adjusted to 6 using 520 g of 20% strength sodium hydroxide solution. The crude product which precipitates out is filtered off and washed with water. After drying in a drying cabinet, 194 g of oxfendazole having a purity of 98.6% remain. The yield is 98.5% of theory, relative to the fenbendazole employed.

The product is white and contains no coloring components. No fenbendazole and no 5-phenylsulfonyl-1H-2-(methoxycarbonylamino)-benzimidazole are found in the product. 750 ml of methanol are recovered virtually quantitatively from the wash water, and can be reused in the next-batch.

The waste water exhibits no fish toxicity and is easily biodegradable.

EXAMPLE 2

186.4 g of fenbendazole are dissolved in 700 ml of methanol, 513 g of 48% strength hydrobromic acid and 400 ml of water at 60° C., and 65.4 g of a 35% strength hydrogen peroxide solution are added at a pH of −0.5. The reaction solution is heated at 60° C. for 7 hours, and 10.0 g of sodium sulfite are then added. After cooling to room temperature, the reaction mixture is introduced into 20% strength sodium hydroxide solution, the product crystallizing out. After drying in vacuo, 194.5 g of oxfendazole remain, corresponding to a yield of 98.8%, relative to the fenbendazole employed. The purity is 98.7%.

EXAMPLE 3

372.8 g of fenbendazole are dissolved in 1,300 ml of methanol under a nitrogen atmosphere, and 500 g of concentrated hydrochloric acid are added. At 40° C., 130 g of a 35% strength hydrogen peroxide solution are added dropwise to this solution within 5 hours, and the mixture is heated at 40° C. for a further 3 hours. After addition of 20 g of sodium sulfite, the pH is adjusted to 4 using 50% strength sodium hydroxide solution, and the precipitated product is filtered off under suction. After washing with water and drying in a vacuum drying cabinet, 390.0 g of oxfendazole are obtained. The purity is 98.6% and the yield 99.0% of theory, relative to the fenbendazole employed.

The prior art on which the application is based is described in greater detail by the comparison examples below.

COMPARISON EXAMPLE 1

Oxidation using hydrogen peroxide in methanol without addition of acid (according to J. Drabowicz et al., Synth. Commun. 11(2), (1981), pp. 1025 ff).

372.8 g of fenbendazole are dissolved in 1,300 ml of methanol, and 130 g of a 35% strength hydrogen peroxide solution are added at 50° C. within 3 hours. After a total reaction time of 7 hours, 10 g of sodium sulfite are added, and the crude product is filtered off after removing 1,000 ml of methanol by distillation.

After washing and drying in a vacuum drying cabinet, 381.0 g of a product having the following composition are filtered off:
43.4% of fenbendazole
29.2% of oxfendazole and
27.3% of 5-phenylsulfonyl-1H-2-(methoxycarbonylamino)-benzimidazole.

The yield is 13.9% of theory, relative to the fenbendazole employed.

COMPARISON EXAMPLE 2

Oxidation using hydrogen peroxide in acetic acid (according to German Offenlegungsschrift No. 2,334,631 and German Offenlegungsschrift No. 2,432,631).

186.4 g of fenbendazole are slurried in 1,600 ml of glacial acetic acid, and 593 ml of a 30% strength hydrogen peroxide solution are added at room temperature. After stirring for 1 hour at room temperature, the solution is introduced into 3,000 ml of water, and the precipitated product is filtered off, washed with water and methanol, and subsequently dried in a vacuum drying cabinet.

132.7 g of oxfendazole having a purity of 91.2%, corresponding to a yield of 67.4%, remain as a crude product. The content of 5-phenylsulfonyl-1H-2-(methoxycarbonylamino)-benzimidazole is 7.2%.

The examples of the process according to the invention show that considerably greater yields (98.5–99% of theory) and better purities (98.6–98.7%) of the products are achieved than in the processes described in the comparison examples.

We claim:

1. A process for the preparation of 5-phenylsulfinyl-1H-2-(methoxycarbonylamino)-benzimidazole through reaction of 5-phenylmercapto-1H-2-(methoxycarbonylamino)benzimidazole with hydrogen peroxide, wherein the reaction is carried out in mineral acid in the presence of one or more aliphatic $C_1$–$C_6$-alcohols.

2. The process as claimed in claim 1, wherein the mineral acid used is hydrochloric acid, hydrobromic acid or phosphoric acid.

3. The process as claimed in claim 1, wherein the solvent used is an aliphatic $C_1$–$C_6$-alkanol.

4. The process as claimed in claim 1, wherein hydrochloric acid and methanol are used.

5. The process as claimed in claim 1, wherein the reaction is carried out at 0° to 80° C.

6. The process as claimed in claim 1, wherein the reaction is carried out at pH −1.0 to 2.0.

7. The process as claimed in claim 1, wherein the reaction is carried out under an inert gas atmosphere.

* * * * *